(12) United States Patent
Nagao

(10) Patent No.: US 11,244,447 B2
(45) Date of Patent: Feb. 8, 2022

(54) MEASUREMENT DEVICE AND COMPUTER READABLE STORAGE MEDIUM

(71) Applicant: Konica Minolta, Inc., Tokyo (JP)

(72) Inventor: Kenji Nagao, Tokorozawa (JP)

(73) Assignee: KONICA MINOLTA, INC., Tokyo (JP)

(*) Notice: Subject to any disclaimer, the term of this patent is extended or adjusted under 35 U.S.C. 154(b) by 103 days.

(21) Appl. No.: 16/692,431

(22) Filed: Nov. 22, 2019

(65) Prior Publication Data

US 2020/0167919 A1    May 28, 2020

(30) Foreign Application Priority Data

Nov. 22, 2018    (JP) .............................. JP2018-218800

(51) Int. Cl.
*G06K 9/00* (2006.01)
*B41M 5/00* (2006.01)
*G06T 7/00* (2017.01)
*A61B 6/00* (2006.01)

(52) U.S. Cl.
CPC ............ *G06T 7/0012* (2013.01); *A61B 6/465* (2013.01); *A61B 6/469* (2013.01); *A61B 6/503* (2013.01); *A61B 6/545* (2013.01); *G06T 2207/30048* (2013.01); *G06T 2207/30061* (2013.01)

(58) Field of Classification Search
USPC ....... 382/100, 103, 107, 128–132, 154, 162, 382/168, 172, 173, 181, 199, 219, 254, 382/274, 276, 286, 305, 189; 378/8, 21, 378/28, 4; 705/3
See application file for complete search history.

(56) References Cited

U.S. PATENT DOCUMENTS

| | | | | |
|---|---|---|---|---|
| 9,044,194 B2* | 6/2015 | Noji | ...................... | A61B 5/0205 |
| 2014/0172457 A1* | 6/2014 | Ueda | ...................... | G16H 30/40 |
| | | | | 705/3 |
| 2015/0092911 A1* | 4/2015 | Noji | ...................... | A61B 5/113 |
| | | | | 378/8 |
| 2017/0025158 A1* | 1/2017 | Miyake | ................ | G06K 9/6269 |
| 2018/0296277 A1* | 10/2018 | Schwartz | ............... | G16H 30/20 |
| 2020/0234448 A1* | 7/2020 | Dai | ........................... | G06T 7/13 |

FOREIGN PATENT DOCUMENTS

JP       2011125385 A       6/2011

* cited by examiner

*Primary Examiner* — Seyed H Azarian
(74) *Attorney, Agent, or Firm* — Cantor Colburn LLP

(57) ABSTRACT

A measurement device including a hardware processor that: extracts a frame image at a time of deep inspiration from a plurality of frame images of a dynamic image obtained by performing radiation imaging of a dynamic state of a chest of a subject; and performs cardiothoracic ratio measurement to the extracted frame image at the time of deep inspiration.

11 Claims, 7 Drawing Sheets

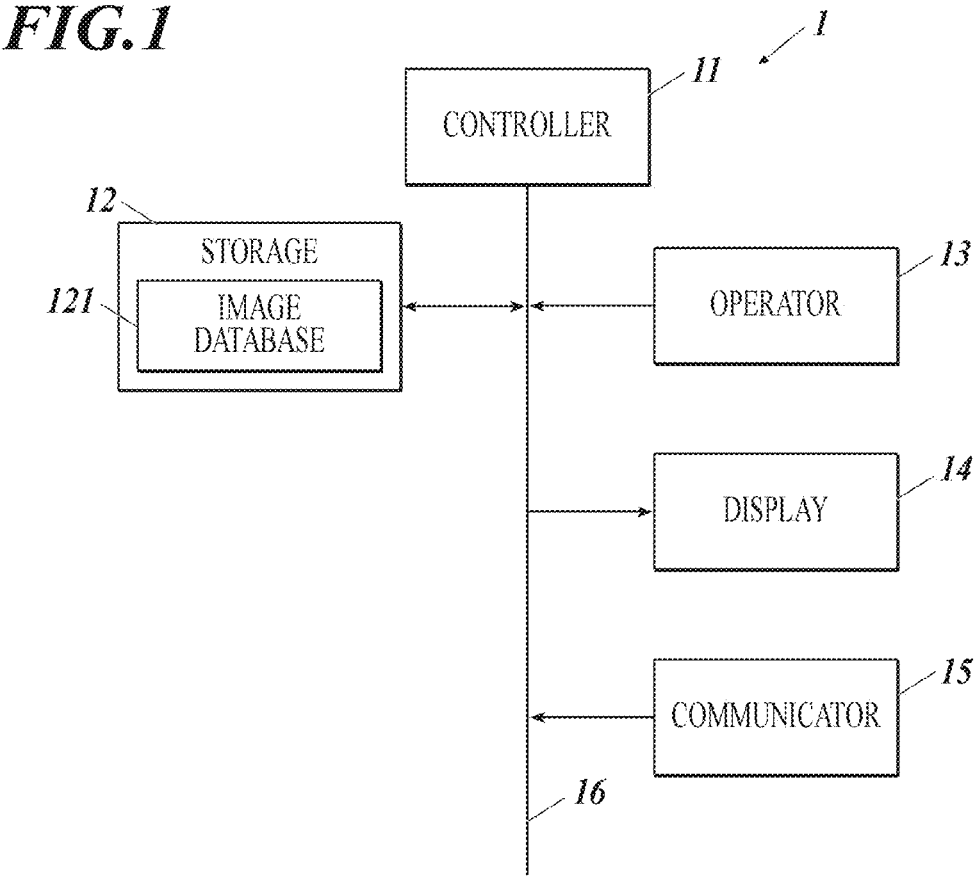
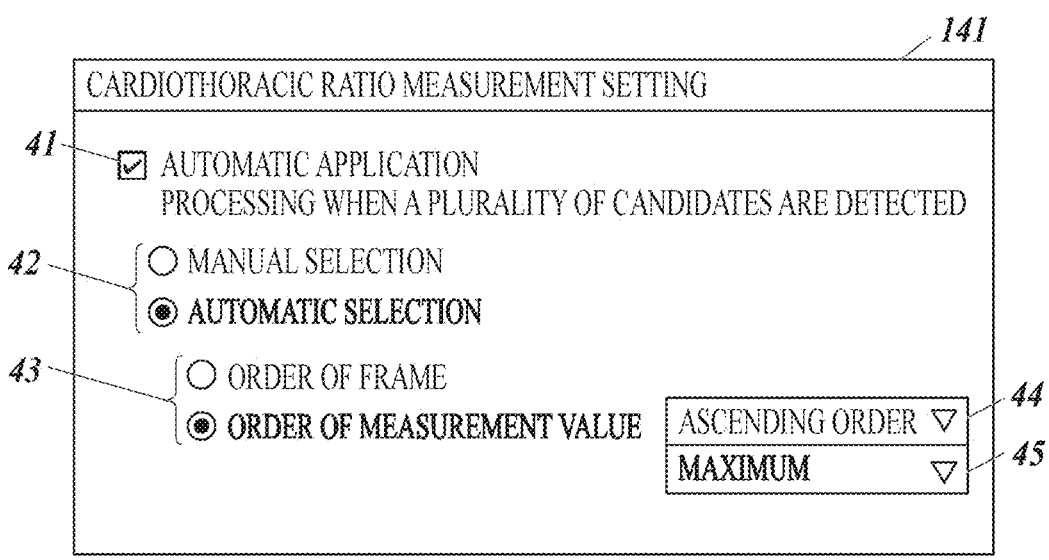

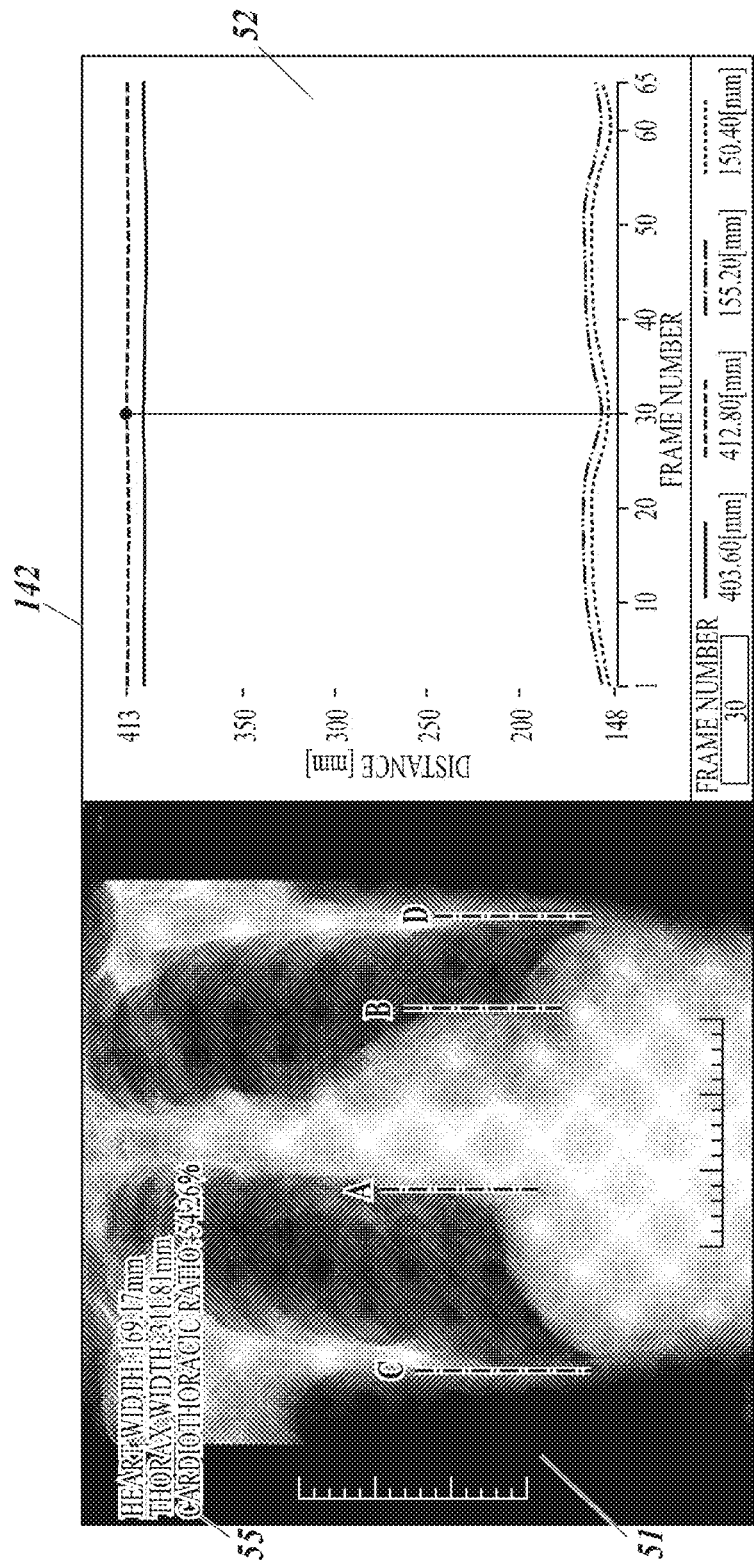

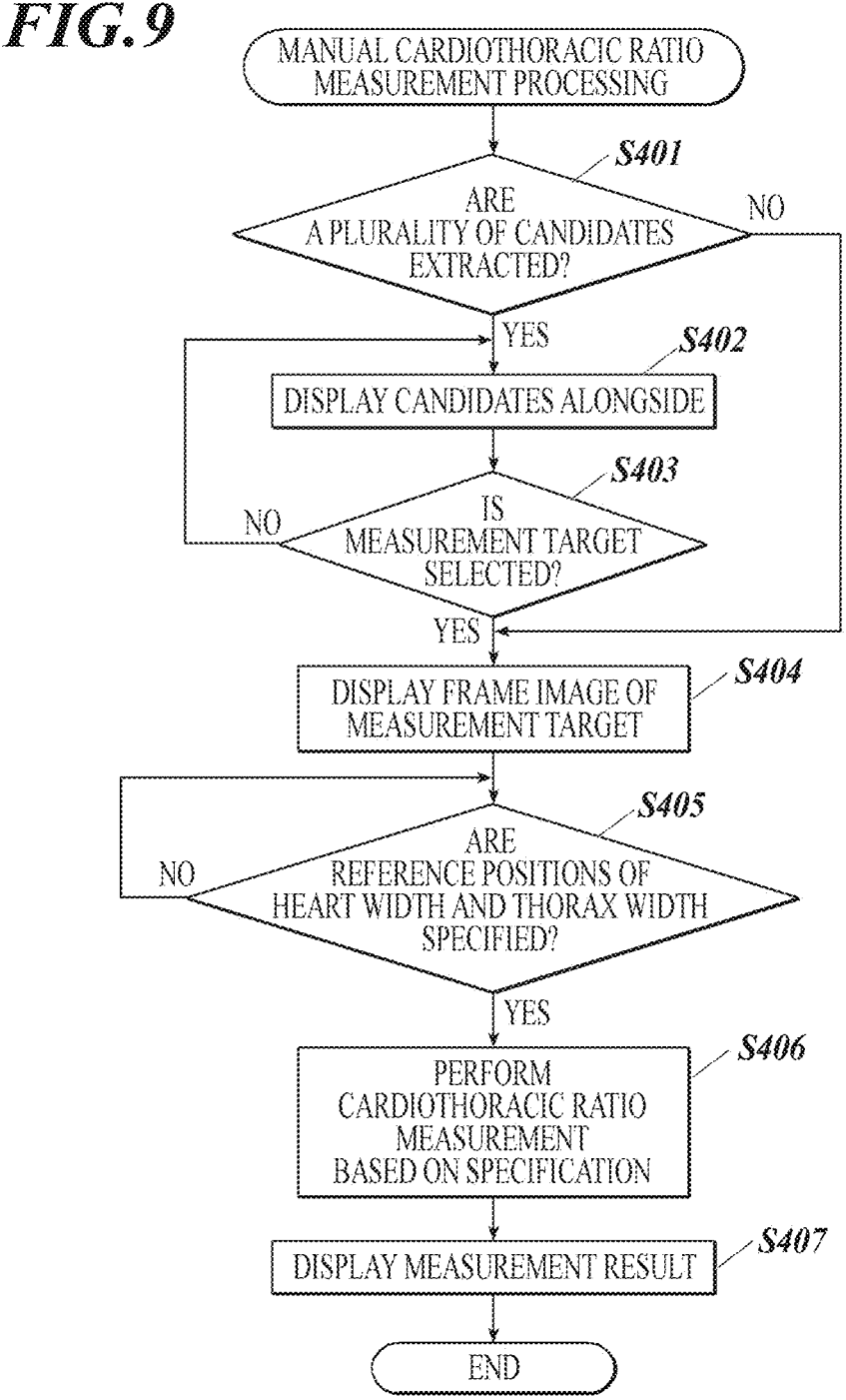

MEASUREMENT DEVICE AND COMPUTER READABLE STORAGE MEDIUM

CROSS-REFERENCE TO RELATED APPLICATION

The present invention claims priority under 35 U.S.C. § 119 to Japanese patent application No. 2018-218800 filed on Nov. 22, 2018, the entire contents of which are incorporated herein by reference.

BACKGROUND

Technological Field

The present invention relates to a measurement device and a computer readable storage medium.

Description of the Related Art

For example, when diagnosis is performed regarding cardiac hypertrophy, hypertrophic cardiomyopathy and the like, a chest of a subject is imaged with radiation, the radiation image obtained by the imaging is used to obtain the width of heart and the width of thorax, and the ratio thereof (cardiothoracic ratio=heart width/thorax width) (CTR) is calculated.

The cardiothoracic ratio (CTR) is obtained generally from the shade of heart shown in a static image which was obtained by radiation imaging. There is a concern that the measurement may not be performed accurately in the static image depending on whether the heart at the moment of imaging is in the contracting state or in the expanding state since the movement of heartbeat is not considered. Thus, there has been suggested to perform cardiothoracic ratio measurement for each of frame images in a dynamic image obtained by performing radiation imaging of a dynamic state to a chest of a subject and selecting an appropriate value to provide information which is more appropriate for diagnosis.

For example, JP 2011-125385A describes providing cardiothoracic ratios at a plurality of points in time by obtaining X-ray image data of a plurality of frames and obtaining the cardiothoracic ratio for each of the frames. JP 2011-125385A also describes controlling a display to display the maximum value of the cardiothoracic ratios obtained for respective frames.

The image to perform the cardiothoracic ratio measurement which is decisive to the diagnosis needs to be an image which was imaged at the time of deep inspiration. In JP 2011-125385A, the cardiothoracic ratio measurement is performed uniformly to all the frame images, and the frame image which has the maximum cardiothoracic ratio is simply extracted from among the frame images. However, the simply-extracted maximum value is not necessarily the cardiothoracic ratio which is really appropriate for the diagnosis (that is, the cardiothoracic ratio at the time of deep inspiration). Moreover, in a dynamic image imaging a plurality of respirations, the number of the series of frame images is several hundreds. The measurement processing is performed for the frame images though most of the measurement values are not necessary, which takes an unnecessary time.

SUMMARY

An object of the present invention is to efficiently perform the cardiothoracic ratio measurement to a more appropriate frame image in the dynamic image.

To achieve at least one of the abovementioned objects, according to an aspect of the present invention, a measurement device reflecting one aspect of the present invention includes a hardware processor that: extracts a frame image at a time of deep inspiration from a plurality of frame images of a dynamic image obtained by performing radiation imaging of a dynamic state of a chest of a subject; and performs cardiothoracic ratio measurement to the extracted frame image at the time of deep inspiration.

According to an aspect of the present invention, a computer readable storage medium reflecting one aspect of the present invention stores a program causing a computer to perform: extracting that is extracting a frame image at a time of deep inspiration from a plurality of frame images of a dynamic image obtained by performing radiation imaging of a dynamic state of a chest of a subject; and measuring that is performing cardiothoracic ratio measurement to the frame image at the time of deep inspiration which is extracted in the extracting.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 1 is a block diagram showing a functional configuration of a measurement device in an embodiment of the present invention;

FIG. 2 is a view showing an example of a setting screen of the cardiothoracic ratio measurement;

FIG. 8 is a view showing an example of the cardiothoracic ratio measurement screen displaying the measurement result; and FIG. 9 is a flowchart showing the flow of manual cardiothoracic ratio measurement processing executed in step S4 in FIG. 3.

DETAILED DESCRIPTION OF EMBODIMENTS

Figure 3:
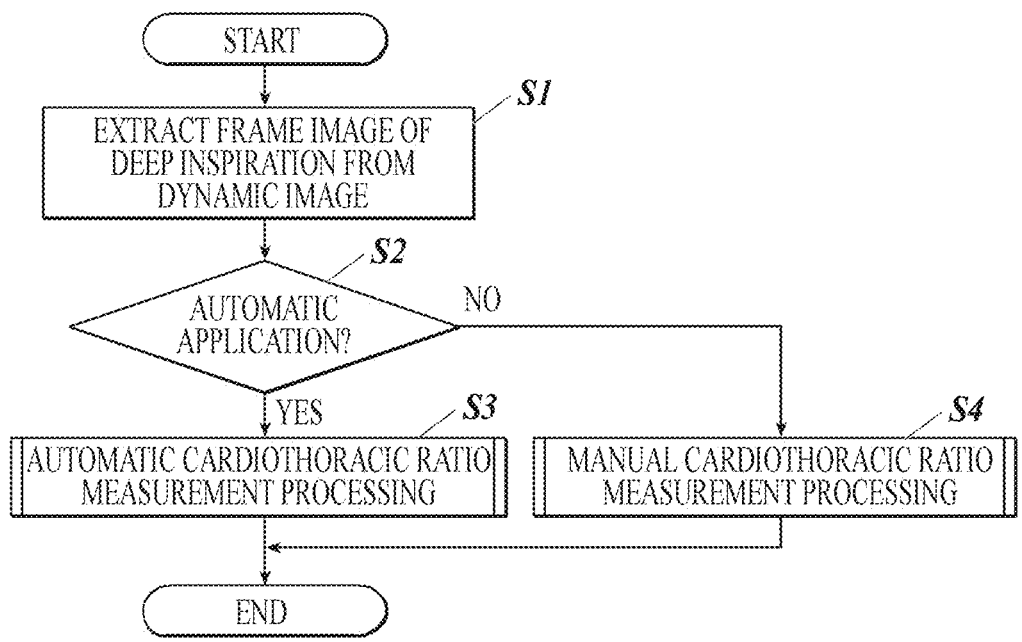
FIG. 3 is a flowchart showing the flow of cardiothoracic ratio measurement processing executed by a controller in FIG. 1.

Hereinafter, one or more embodiments of the present invention will be described with reference to the drawings. However, the scope of the invention is not limited to the disclosed embodiments or illustrated examples.

[Configuration of Measurement Device 1]

First, the configuration of a measurement device 1 according to the present invention will be described.

The measurement device 1 is a device which measures the cardiothoracic ratio from the dynamic image obtained by dynamic imaging of the chest of a subject.

The dynamic imaging is obtaining a plurality of images showing the dynamic state of the subject by repeatedly emitting pulsed radiation such as X-rays at predetermined time intervals (pulse emission) or continuously emitting radiation at a low dose rate without interruption (continuous emission), to a target site (in the embodiment, chest) of the subject. The series of images obtained by the dynamic imaging is called a dynamic image. Each of the plurality of images forming the dynamic image is referred to as a frame image.

FIG. 1 is a block diagram showing the functional configuration of the measurement device 1. As shown in FIG. 1, the measurement device 1 is configured by including a controller 11, a storage 12, an operator 13, a display 14, a communicator 15 and the like, and the components are connected to each other via a bus 16.

The controller 11 is configured by including a CPU (Central Processing Unit), a RAM (Random Access Memory), and the like. In response to the operation of the operator 13, the CPU of the controller 11 reads out system programs and various types of processing programs stored in the storage 12, loads them to the RAM, and integrally controls the operations of the components in the measurement device 1 in accordance with the loaded programs.

The storage 12 is configured by including a nonvolatile semiconductor memory, a hard disk, and the like. The storage 12 stores the system programs and the various types of programs to be executed by the controller 11, and data such as a parameter necessary to execute the processing by the program. For example, the storage 12 stores a program for executing after-mentioned cardiothoracic ratio measurement processing. The various types of programs are stored in a form of readable program code, and the controller 11 sequentially executes the operation according to the program code.

The storage 12 has an image database (image DB) 121. The image database 121 stores, for example, patient information (such as the patient ID, patient name, height, weight, age and sex), test information (such as the test ID, test date, imaging site (in the embodiment, chest) and imaging direction (front side, lateral side)), and image information (such as the image ID, radiation emission condition, image reading condition and number indicating the order of imaging (frame number)) so as to be associated with each of the frame images of the dynamic image transmitted from an imaging device not shown in the drawings.

The operator 13 is configured by including a keyboard including a cursor key, numeral input keys, various function keys and the like, and a pointing device such as a mouse. The operator 13 outputs, to the controller 11, an instruction signal which was input by a key operation to the keyboard and a mouse operation performed by the user. The operator 13 may include a touch panel on the display screen of the display 14. In this case, the operator 13 outputs an instruction signal input via the touch panel to the controller 11.

The display 14 is configured by including a monitor such as an LCD (Liquid Crystal Display) and a CRT (Cathode Ray Tube), and displays the instruction input from the operator 13, data and the like in accordance with the instruction of the display signal input from the controller 11.

The communicator 15 includes a LAN adapter, a modem, a TA (Terminal Adapter) and the like, and controls data transmission and reception with an external device such as the imaging device which is connected to the communication network and not shown in the drawings.

[Operation of Measurement Device 1]

Next, the operation of the measurement device 1 in the embodiment will be described.

In the measurement device 1, the controller 11 controls the display 14 to display a setting screen 141 shown in FIG. 2 in accordance with the operation to the operator 13 by the user, and receives various types of settings for cardiothoracic ratio measurement from the setting screen 141.

As shown in FIG. 2, in the setting screen 141, there are provided a check box 41 for selecting whether to automatically apply the cardiothoracic ratio measurement, a radio button 42 for selecting whether to manually select (manual selection) or automatically select (automatic selection) the frame image to be the measurement target (frame image which is the source of measurement result) when a plurality of candidates are extracted as the frame image which is the candidate of the target of the cardiothoracic ratio measurement, and a radio button 43 for selecting whether to select the frame image by giving priority to the order of frame number or select the frame image by giving priority to the order of measurement value when the automatic selection is selected. There are also provided a pull-down menu 44 for specifying whether to select the frame image in the ascending order or in the descending order when the radio button 43 for selecting the frame image in the order of frame is pressed, and a pull-down menu 45 for specifying the condition (such as maximum value, minimum value or average value) to be met by the measurement value selected as the cardiothoracic ratio of the subject when the order of measurement value is selected.

The radio button 42 can be input only when the check box 41 is checked. The radio button 43 can be input only when the automatic selection is selected in the radio button 42. The pull-down menu 44 can be input only when the order of frame is selected in the radio button 43, and the pull-down meu 45 can be input only when the order of measurement value is selected in the radio button 43.

The setting information input from the setting screen 141 is stored in the storage 12 by the controller 11. When the dynamic image which is the measurement target of the cardiothoracic ratio is selected from the dynamic images stored in the image database 121 by the operator 13, the controller 11 executes the cardiothoracic ratio measurement processing (see FIG. 3) by the cooperation between the controller 11 and the program stored in the storage 12, and measures the cardiothoracic ratio on the basis of the setting information stored in the storage 12.

Hereinafter, with reference to FIG. 3, the cardiothoracic ratio measurement processing will be described.

First, the controller 11 extracts the frame image at the time of deep inspiration from the selected dynamic image (step S1).

In order to perform the cardiothoracic ratio measurement which is decisive to the diagnosis, the measurement needs to be performed with the image which was imaged at the time of deep inspiration. Thus, in step S1, the frame image at the time of deep inspiration is extracted as the frame image which is the target of the cardiothoracic ratio measurement. In the embodiment, the time of deep inspiration indicates the point in time of the maximal inspiratory level by deep breathing.

In step S1, the controller 11 first extracts the outer edge of each pulmonary region in the lead frame image, for example. The pulmonary region can be extracted by using a known method. For example, as described in JP H8-335271

(A), the lead frame image is scanned sequentially in the horizontal direction and the vertical direction to create a profile of signal value in each of the directions, and the outer edge of each pulmonary region is extracted on the basis of the inflection point in the profile.

Figure 4A:
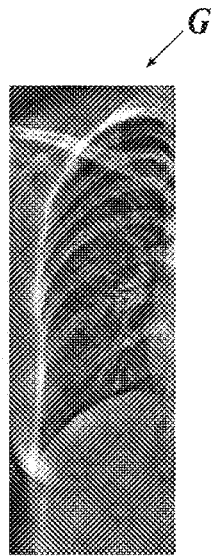
FIG. 4A is a view showing a medical image of extraction target of the positions of lung apex and diaphragm.
Figure 4B:
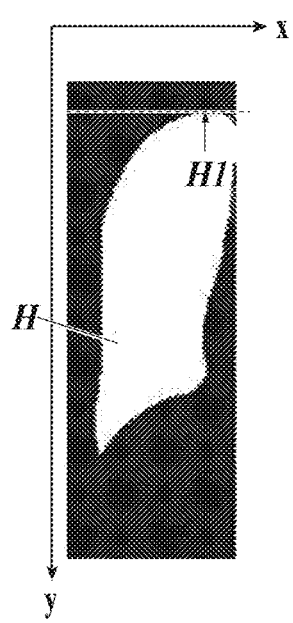
FIG. 4B is a view for explaining an extraction method of the positions of the lung apex and the diaphragm in FIG. 4A.
Figure 4C:
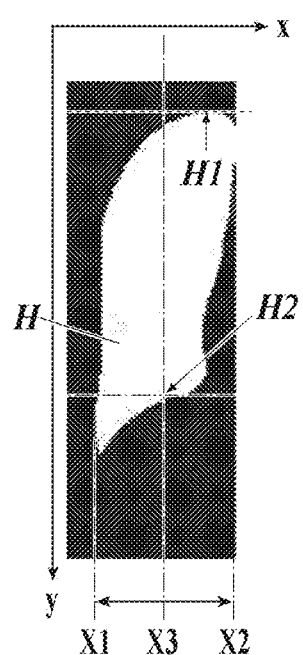
FIG. 4C is a view for explaining the extraction method of the position of the diaphragm in FIG. 4A.

Next, the controller 11 obtains the position of lung apex in the pulmonary region and the position of diaphragm in each of the frame images. For example, the point having the minimum y coordinate in the pulmonary region (H) extracted from the lead frame image (G) shown in FIG. 4A is automatically extracted as the position (H1) of the lung apex (see FIG. 4B). The point (H2) is automatically extracted as the position of diaphragm, the point (H2) having the maximum y coordinate and the central x coordinate (X3) of the x coordinate range (X1-X2) where the pulmonary region (H) exists (see FIG. 4C). Alternatively, the lead frame image may be displayed on the display 14 so that the user directly specifies the positions of lung apex and diaphragm by the operator 13. By tracing the positions of lung apex and diaphragm obtained from the lead frame image with respect to the remaining frame images with the pattern matching, the positions of lung apex and diaphragm in each of the frame images are obtained. Though FIG. 4A to FIG. 4C show only the right lung, the same also applies to the left lung.

The controller 11 extracts the frame image having the largest distance in the vertical direction between the position of the lung apex and the position of the diaphragm as the frame image at the time of deep inspiration.

The extraction method of the frame image at the time of deep inspiration is not limited to the above-mentioned method. For example, the controller 11 may obtain any other feature amount, for example, an area of the pulmonary region in each of the frame images, and the frame image having the largest area may be extracted as the frame image at the time of deep inspiration.

The controller 11 refers to the storage 12, and determines whether the automatic application of the cardiothoracic ratio measurement is set (step S2).

If the controller 11 determines that the automatic application of the cardiothoracic ratio measurement is set (step S2; YES), the controller 11 executes automatic cardiothoracic ratio measurement processing (step S3).

Figure 5:
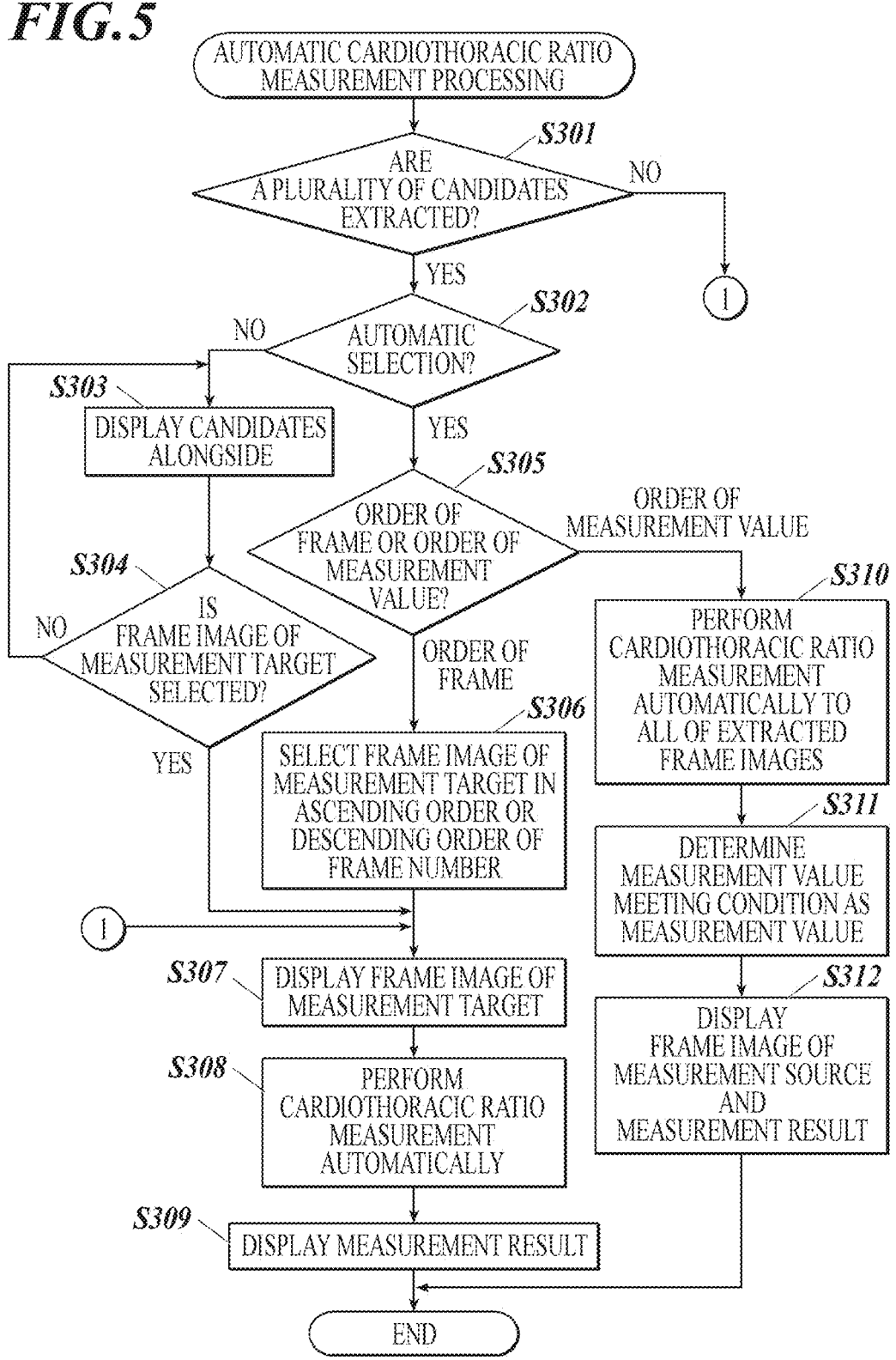
FIG. 5 is a flowchart showing the flow of automatic cardiothoracic ratio measurement processing executed in step S3 in FIG. 3.

FIG. 5 is a flowchart showing the flow of the automatic cardiothoracic ratio measurement processing. The automatic cardiothoracic ratio measurement processing is executed by the cooperation between the controller 11 and the program stored in the storage 12.

The controller 11 first determines whether a plurality of frame images at times of deep inspiration (referred to as a plurality of candidates) were extracted in step S1 (step S301). For example, a plurality of frame images at the times of deep inspiration are extracted in step S1 in a case of a dynamic image obtained by holding the breath at the time of deep inspiration and in a case of a dynamic image imaging for a plurality of respiration periods.

If the controller 11 determines that a plurality of candidates were not extracted (step S301; NO), the controller 11 proceeds to step S307 with the extracted frame image as the measurement target.

If the controller 11 determines that a plurality of candidates were extracted in step S1 (step S301; YES), the controller 11 refers to the storage 12 and determines whether the automatic selection of the frame image of the measurement target (frame image which is to be the source of the measurement result) is set (step S302).

If the controller determines that the automatic selection is not set (step S302; NO), the controller 11 controls the display 14 to display alongside the plurality of frame images extracted in step S1 (step S303). When the frame image of the measurement target is selected from among the displayed plurality of frame images with the operation to the operator 13 by the user (step S304; YES), the controller 11 proceeds to step S307.

If the controller 11 determines that the automatic selection is set (step S302; YES), the controller 11 refers to the storage 12, and determines whether the frame image of the measurement target (frame image which is to be the source of the measurement result) is set to be selected in the order of frame or set to be selected in the order of measurement value (step S305).

If the controller 11 determines that the frame image of the measurement target is set to be selected in the order of frame (step S305; order of frame), the controller 11 selects, as the frame image of the measurement target of cardiothoracic ratio, the frame image having the smallest frame number (in the case of ascending order) or the frame image having the largest frame number (in the case of descending order) from among the frame images of deep inspiration level selected in step S1 (step S306). The controller 11 then proceeds to step S307.

In step S307, the controller 11 controls the display 14 to display the cardiothoracic ratio measurement screen 142 including the frame image of the measurement target (step S307).

Figure 6:
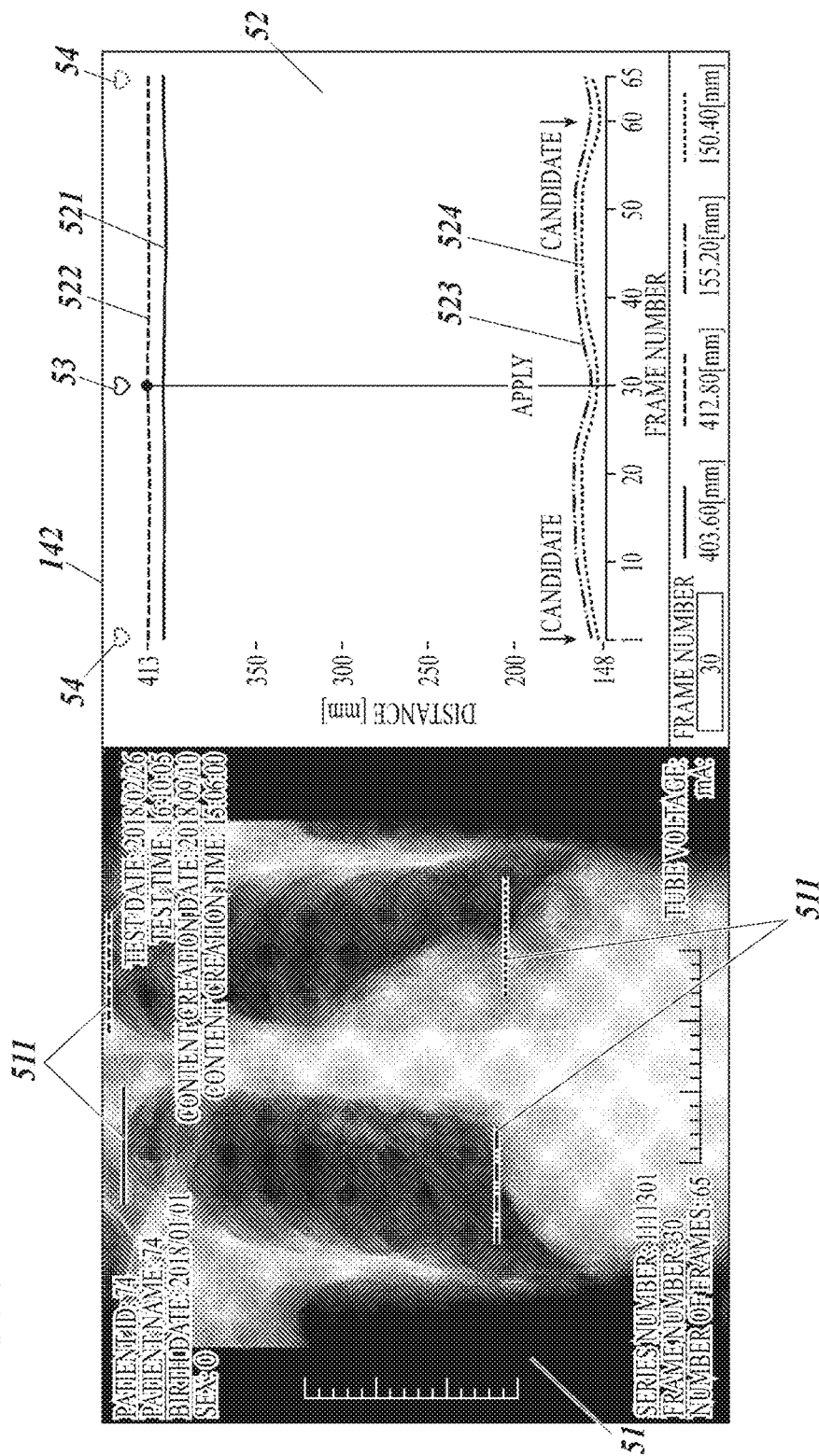
FIG. 6 is a view showing an example of a cardiothoracic ratio measurement screen.

FIG. 6 is a view showing an example of the cardiothoracic ratio measurement screen 142. As shown in FIG. 6, an image display region 51 and a graph display region 52 are provided in the cardiothoracic ratio measurement screen 142. The frame image of the measurement target (frame image at the time of deep inspiration) is displayed in the image display region 51. The annotation lines 511 showing the positions of lung apexes and diaphragm are displayed on the frame image. The graphs showing the change over time in the positions of lung apexes and diaphragm in the dynamic image of the measurement target are displayed in the graph display region 52. In the graph display region 52, the lines 521, 522, 523 and 524 respectively show the change over time in the positions of the right lung apex, the left lung apex, the right diaphragm and the left diaphragm. On the graph, there are displayed the marker 53 showing the position of the frame image to which the cardiothoracic ratio measurement is applied and the markers 54 showing the positions of candidate frame images in a case where the candidate frame images exist. There are also displayed in the lower left of the graph the frame number of frame image of the measurement target and the coordinates of the positions of lung apexes and diaphragm.

Next, the controller 11 performs the cardiothoracic ratio measurement automatically to the frame image of the measurement target (step S308).

Figure 7:
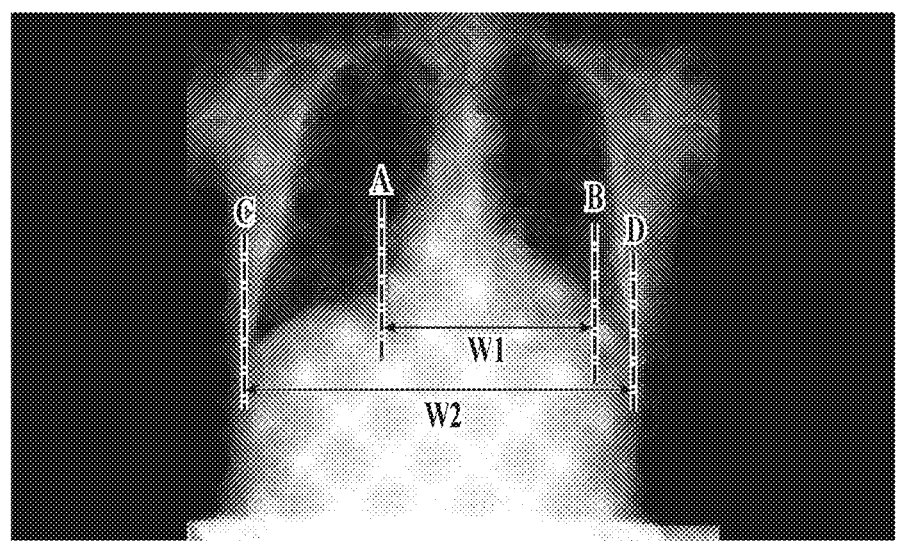
FIG. 7 is a view for explaining the heart width and the thorax width.

In step S308, the controller 11 extracts the outline of the heart region in the frame image of the measurement target and measures the heart width W1 on the basis of the outline of the heart region. For example, as shown in FIG. 7, with the left and right outermost positions of the heart outline as reference positions A and B, the length between A and B (length in the horizontal direction) is calculated as the heart width W1. As the extraction method of the heart region, there may be used any known method such as template matching using a template image of heart, for example. The controller 11 extracts the outline of the pulmonary region of the frame image of the measurement target, and measures the thorax width W2 on the basis of the outline of the pulmonary regions. For example, as shown in FIG. 7, with the outermost position of the outline of one pulmonary region and the outermost position of the outline of the other pulmonary region as reference positions C and D, the length between C and D (length in the horizontal direction) is calculated as the thorax width W2. Then the controller 11 calculates W1/W2 as the cardiothoracic ratio.

When the cardiothoracic ratio measurement is finished, the controller 11 controls the display 14 to display the measurement result of the cardiothoracic ratio in the cardiothoracic ratio measurement screen 142 (step S309), and ends the automatic cardiothoracic ratio measurement processing.

FIG. 8 shows an example of the cardiothoracic ratio measurement screen 142 displaying the frame image on which the reference positions A to D of the measurement are displayed and the measurement result 55.

The user may be allowed to make a minor adjustment with the operator 13 to the reference positions A to D displayed on the frame image in the cardiothoracic ratio measurement screen 142. In a case where the minor adjustment was made, the controller 11 may measure the cardiothoracic ratio again by calculating the heart width W1 and the thorax width W2 on the basis of the reference positions A to D which were adjusted.

On the other hand, in step S303, if the controller 11 determines that the order of measurement value was selected (step S303; order of measurement value), the controller 11 performs the cardiothoracic ratio measurement automatically to all of the frame images at times of deep inspiration extracted in step S1 (step S310), and determines the measurement value that meets the condition set in the storage 12 as the measurement value of the cardiothoracic ratio of the subject (step S311). The measurement value that meets the condition includes the measurement value which is closest to the condition.

The controller 11 controls the display 14 to display the determined measurement value as the measurement result in the cardiothoracic ratio measurement screen 142 together with the frame image which is the measurement source of the measurement value (step S312), and ends the automatic cardiothoracic ratio measurement processing. The cardiothoracic ratio measurement screen 142 displayed in step S312 is similar to that shown in FIG. 8.

In step S2 in FIG. 3, if the controller 11 determines that the automatic application of the cardiothoracic ratio measurement is not set (step S2; NO), the controller 11 executes the manual cardiothoracic ratio measurement processing (step S4).

FIG. 9 is a flowchart showing the flow of the manual cardiothoracic ratio measurement processing. The manual cardiothoracic ratio measurement processing is executed in the cooperation between the controller 11 and the program stored in the storage 12.

The controller 11 first determines whether a plurality of frame images (referred to as a plurality of candidates) at times of deep inspiration were extracted in step S1 (step S401).

If the controller 11 determines that the plurality of candidates are not extracted (step S401; NO), the controller 11 proceeds to step S404 with the extracted frame image as the measurement target.

If the controller 11 determines that the plurality of candidates were extracted in step S1 (step S401; YES), the controller 11 controls the display 14 to display alongside the plurality of frame images which were extracted in step S1 (step S402). If the frame image of measurement target is selected from among the displayed plurality of frame images by the operation to the operator 13 by the user (step S403; YES), the controller 11 proceeds to step S404.

In step S404, the controller 11 controls the display 14 to display the cardiothoracic ratio measurement screen 142 including the frame image of the measurement target (step S404).

Though the cardiothoracic ratio measurement screen 142 displayed in step S404 is similar to the cardiothoracic ratio measurement screen 142 shown in FIG. 6, the cardiothoracic ratio measurement screen 142 displayed in step S404 has the following additional functions, for example.

For example, a heart position input button for instructing input of two reference positions of the heart width W1 is provided in the image display region 51, and when the heart position input button is pressed with the operator 13 to specify two points by the image display region 51, the controller 11 sets the specified two points as the reference positions of the heart width. Similarly, a thorax reference position input button for instructing input of two reference positions of the thorax width W2 is provided in the image display region 51, and when the thorax reference position input button is pressed with the operator 13 to specify two points by the image display region 51, the controller 11 sets the specified two points as the reference positions of the thorax width.

When one point on the time axis (horizontal axis) of the graph in the graph display region 52 is specified with the operator 13, the controller 11 displays a marker 53 showing the position of the frame image to which the cardiothoracic ratio measurement is applied at the position specified on the graph, and switches and displays the frame image corresponding to the specified position in the image display region 51. That is, the user can change the frame image of the measurement target of the cardiothoracic ratio. In a case where the specified frame image is not the frame image at the time of deep inspiration, it is preferable to display a warning message in the cardiothoracic ratio measurement screen 142 or output the warning message by sound, the warning message being a message for calling user's attention to that the specified frame image is not the frame image at the time of deep inspiration. An alarm sound may be output. The controller 11 may measure the cardiothoracic ratio automatically for the frame image corresponding to the marker 53 when the marker 53 is pressed with the operator 13.

The controller 11 determines whether the reference positions of the heart width and the reference positions of the thorax width were specified with the operator 13 (step S405).

If the controller 11 determines that the reference positions of the heart width and the reference positions of the thorax width were specified with the operator 13 (step S405; YES), the controller 11 automatically measures the cardiothoracic ratio on the basis of the specified reference positions (step S406). That is, the controller 11 measures, as the heart width W1, the length in the horizontal direction between the specified reference positions of the heart width, measures, as the thorax width W2, the length in the horizontal direction between the specified reference positions of the thorax width, and calculates W1/W2 as the cardiothoracic ratio.

When the cardiothoracic ratio measurement is finished, the controller 11 controls the display 14 to display the measurement result of the cardiothoracic ratio in the cardiothoracic ratio measurement screen 142 (step S407), and ends the manual cardiothoracic ratio measurement processing.

The cardiothoracic ratio measurement screen 142 displayed in step S407 is similar to that shown in FIG. 8.

The measurement result of the cardiothoracic ratio by the cardiothoracic ratio measurement processing is stored in the image database 121 so as to be associated with the dynamic image (frame image of the measurement source) by the controller 11.

As described above, according to the measurement device 1, the controller 11 extracts a frame image at a time of deep inspiration from a plurality of frame images of a dynamic image of a chest, and performs cardiothoracic ratio measurement to the extracted frame image at the time of deep inspiration. Accordingly, since the cardiothoracic ratio measurement is performed only to the frame image at the time of deep inspiration which is decisive to the diagnosis in the dynamic image, it is possible to efficiently perform the cardiothoracic ratio measurement to the appropriate frame image.

The controller 11 extracts the pulmonary regions from each of the plurality of frame images in the dynamic image, calculates a feature amount of the extracted pulmonary region, and extracts the frame image at the time of deep inspiration based on the calculated feature amount. Accordingly, it is possible to extract the frame image at the time of deep inspiration on the basis of the change in the feature amount of the pulmonary region.

The controller 11 controls a display 14 to display the extracted frame image at the time of deep inspiration. Accordingly, the user can confirm the frame image which is the target of the cardiothoracic ratio measurement.

The controller 11 controls the display 14 to display a graph showing a change over time of a feature amount calculated from each of the plurality of frame images, and controls the display 14 to display a marker at a position of the frame image that is a measurement target on the graph. Accordingly, the user can recognize the state in the change over time of the calculated feature amount, in which the frame image to be the measurement target was imaged.

The controller 11 measures a heart width and a thorax width by analyzing the extracted frame image at the time of deep inspiration, and measures a cardiothoracic ratio based on the heart width and the thorax width which were measured. Accordingly, it is possible to save user's trouble of setting the reference positions of the heart width and the thorax width.

In a case where a plurality of frame images at times of deep inspiration are extracted from the dynamic image, the controller 11 selects the frame image to be a target of the cardiothoracic ratio measurement from among the extracted plurality of frame images.

For example, the controller 11 selects a frame image, which was selected by a user operation, as the frame image to be the target of the cardiothoracic ratio measurement. Accordingly, it is possible to select, as the measurement target, the frame image desired by the user such as the frame image in the same state as the heartbeat state of the heart of the previous imaging from among the frame images at the times of deep inspiration, for example.

For example, the controller 11 automatically selects the frame image to be the target of the cardiothoracic ratio measurement from among the plurality of frame images in accordance with a priority that is set in advance. For example, the controller 11 selects the frame image to be the measurement target in an ascending order or a descending order of a frame number that is provided to each of the plurality of frame images. Accordingly, it is possible to save user's trouble of selecting the measurement target.

In a case where a plurality of frame images at times of deep inspiration were extracted, the controller 11 obtains a measurement value by performing the cardiothoracic ratio measurement to each of the extracted plurality of frame images, and determines a measurement value that meets a condition set in advance as a cardiothoracic ratio of the subject. Accordingly, it is possible to obtain the measurement value that meets a predetermined condition (for example, maximum, minimum, average value or the like of the calculated measurement values) as the cardiothoracic ratio of the subject. Also, it is possible to calculate and compare the measurement value of the same condition as the condition of previous imaging by setting the same condition as the condition of previous imaging and performing the measurement, for example.

The controller 11 performs control to output a warning that calls attention when a frame image different from the extracted frame image at the time of deep inspiration is selected as a measurement target of a cardiothoracic ratio by a user operation. Accordingly, it is possible to suppress the measurement of cardiothoracic ratio in the frame image other than the frame image at the time of deep inspiration.

The description in the above embodiment is a preferred example of the present invention, and does not limit the present invention.

For example, in the embodiment, a feature amount (for example, positions and distance of the lung apex and the diaphragm) for extracting the frame image at the time of deep inspiration is calculated from each of the frame images of the dynamic image in the measurement device. However, the frame image at the time of deep inspiration may be calculated by using the data of the feature amount of each of the frame images which was calculated by any other device.

The embodiment has been described by taking, as an example, a case where the dynamic image is stored in the storage inside the measurement device. However, the dynamic image may be stored in any other device such as an image server. The cardiothoracic ratio measurement processing may be performed to a dynamic image which was obtained from the any other device. For example, the interpretation terminal of PACS (Picture Archiving and Communication System) may have a function of executing the cardiothoracic ratio measurement processing so that the cardiothoracic ratio measurement processing is performed to the dynamic image obtained from the server of PACS in the interpretation terminal. Also in this case, the feature amount for extracting the frame image at the time of deep inspiration may be calculated from each of the frame images in advance and the dynamic image may be accompanied with the calculated feature amounts. The server may have the function of executing the cardiothoracic ratio measurement processing, and the operation and displaying may be performed via the interpretation terminal.

The above description discloses an example of using a hard disk, a semiconductor nonvolatile memory and the like as the computer readable medium of the program according to the present invention. However the present invention is not limited to the example. A portable storage medium such as a CD-ROM can be applied as other computer readable medium. A carrier wave is also applied as a medium providing the program data according to the present invention via a communication line.

As for the other detailed configurations and detailed operations of the measurement device, modifications can be made as needed within the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A measurement device comprising a hardware processor that:
   extracts, based on a feature amount of a pulmonary region, a frame image at a time of deep inspiration from a plurality of frame images of a dynamic image obtained by performing radiation imaging of a dynamic state of a chest of a subject, the feature amount including a minimum y coordinate and a point having the a maximum y coordinate and a central x coordinate of a x coordinate range in the pulmonary region; and
   performs cardiothoracic ratio measurement to the extracted frame image at the time of deep inspiration,
   wherein the hardware processor controls a display to display the extracted frame image, and
   the hardware processor controls the display to display a graph showing a change over time of the feature amount calculated from each of the plurality of frame images, and controls the display to display a marker at a position of the frame image that is a measurement target on the graph.

2. The measurement device according to claim 1, wherein the hardware processor extracts the pulmonary region from each of the plurality of frame images, calculates the feature amount of the extracted pulmonary region, and extracts the frame image at the time of deep inspiration based on the calculated feature amount.

3. The measurement device according to claim 1, wherein the hardware processor measures a heart width and a thorax width by analyzing the extracted frame image, and measures a cardiothoracic ratio based on the heart width and the thorax width that are measured.

4. The measurement device according to claim 1, wherein, when a plurality of frame images at times of deep inspiration are extracted, the hardware processor selects the frame image to be a target of the cardiothoracic ratio measurement from among the extracted plurality of frame images.

5. The measurement device according to claim 4, wherein the hardware processor selects a frame image, which is selected by a user operation, as the frame image to be the target of the cardiothoracic ratio measurement.

6. The measurement device according to claim 4, wherein the hardware processor selects the frame image to be the target of the cardiothoracic ratio measurement from among the plurality of frame images in accordance with a priority that is set in advance.

7. The measurement device according to claim 6, wherein the priority is an ascending order or a descending order of a frame number that is provided to each of the plurality of frame images.

8. The measurement device according to claim 1, wherein, when a plurality of frame images at times of deep inspiration are extracted, the hardware processor obtains a measurement value by performing the cardiothoracic ratio measurement to each of the extracted plurality of frame images, and determines a measurement value that meets a condition set in advance as a cardiothoracic ratio of the subject.

9. The measurement device according to claim 1, wherein the hardware processor performs control to output a warning that calls attention when a frame image different from the extracted frame image at the time of deep inspiration is selected as a measurement target of a cardiothoracic ratio by a user operation.

10. A non-transitory computer readable storage medium storing a program causing a computer to perform:
    extracting that is extracting, based on a feature amount of a pulmonary region, a frame image at a time of deep inspiration from a plurality of frame images of a dynamic image obtained by performing radiation imaging of a dynamic state of a chest of a subject, the feature amount including a minimum y coordinate and a point having the a maximum y coordinate and a central x coordinate of a x coordinate range in the pulmonary region;
    measuring that is performing cardiothoracic ratio measurement to the frame image at the time of deep inspiration which is extracted in the extracting; and
    controlling that is controlling a display to display the extracted frame image,
    wherein the controlling includes controlling the display to display a graph showing a change over time of the feature amount calculated from each of the plurality of frame images, and controlling the display to display a marker at a position of the frame image that is a measurement target on the graph.

11. A measurement device comprising a hardware processor that:
    extracts, based on a feature amount of a pulmonary region, a frame image at a time of deep inspiration from a plurality of frame images of a dynamic image obtained by performing radiation imaging of a dynamic state of a chest of a subject, the feature amount being a distance in a vertical direction between a position of a lung apex and a position of a diaphragm; and
    performs cardiothoracic ratio measurement to the extracted frame image at the time of deep inspiration,
    wherein the hardware processor controls a display to display the extracted frame image, and
    the hardware processor controls the display to display a graph showing a change over time of the feature amount calculated from each of the plurality of frame images, and controls the display to display a marker at a position of the frame image that is a measurement target on the graph.

* * * * *